(12) United States Patent
Hochstrasser et al.

(10) Patent No.: US 7,754,436 B2
(45) Date of Patent: *Jul. 13, 2010

(54) DIAGNOSTIC ASSAY FOR STROKE

(75) Inventors: Denis Francois Hochstrasser, Geneva (CH); Jean-Charles Sanchez, Geneva (CH); Catherine Gabrielle Zimmerman, Geneva (CH)

(73) Assignee: Electrophorectics Limited, Cobham, Surrey (GB)

( * ) Notice: Subject to any disclaimer, the term of this patent is extended or adjusted under 35 U.S.C. 154(b) by 425 days.

This patent is subject to a terminal disclaimer.

(21) Appl. No.: 11/536,283

(22) Filed: Sep. 28, 2006

(65) Prior Publication Data

US 2007/0134726 A1  Jun. 14, 2007

Related U.S. Application Data

(63) Continuation-in-part of application No. 10/165,127, filed on Jun. 7, 2002, now Pat. No. 7,144,705, which is a continuation of application No. PCT/EP00/12227, filed on Dec. 4, 2000.

(30) Foreign Application Priority Data

Dec. 10, 1999  (GB) ................................ 9929140.3

(51) Int. Cl.
*G01N 33/53* (2006.01)
*G01N 33/537* (2006.01)

(52) U.S. Cl. .......................... 435/7.1; 435/7.4; 436/501; 436/517; 436/548; 436/15; 436/16; 436/71; 436/811; 530/359

(58) Field of Classification Search ..................... 435/6, 435/7.1, 7.2, 7.4, 7.92, 7.94, 970, 973, 287.2; 436/501, 514, 528, 530, 548, 13, 15, 71, 436/172, 517, 16; 530/359

See application file for complete search history.

(56) References Cited

U.S. PATENT DOCUMENTS

| | | | |
|---|---|---|---|
| 5,710,008 A | 1/1998 | Jackowski | 435/7.4 |
| 7,368,247 B2 * | 5/2008 | Hochstrasser et al. | 435/7.1 |
| 2007/0042425 A1 * | 2/2007 | Hochstrasser et al. | 435/7.1 |
| 2008/0220013 A1 * | 9/2008 | Hochstrasser et al. | 435/7.1 |

FOREIGN PATENT DOCUMENTS

| | | |
|---|---|---|
| EP | 09/62878 | 12/1999 |
| WO | 97/35878 | 10/1997 |

(Continued)

OTHER PUBLICATIONS

Sellner et al., Developmental Role of Fatty Acid-Binding Proteins in Mouse Brain, Development Brain Research 89: 33-46 (1995).*

(Continued)

*Primary Examiner*—Gailene R Gabel
(74) *Attorney, Agent, or Firm*—Arent Fox LLP

(57) ABSTRACT

Heart and brain fatty acid binding proteins (H-FABP, B-FABP) are markers for stroke. The invention provides a diagnostic assay for either of these markers, preferably by ELISA using a anti-H-FABP or B-FABP antibody. Since H-FABP is also a marker for acute myocardial infarction (AMI), to distinguish stroke from AMI requires an assay specific to AMI, e.g. using troponin-1 or CK-MB as a marker, also to be carried out.

6 Claims, 1 Drawing Sheet

FOREIGN PATENT DOCUMENTS

| | | |
|---|---|---|
| WO | 98/45444 | 10/1998 |
| WO | WO 98/45440 | * 10/1998 |
| WO | 98/57171 | 12/1998 |

OTHER PUBLICATIONS

Fujii et al., Increased Renal FABP in spontaneously hypertensive rats, Journal of Hypertension 6: 671-675 (1988).*

Pelsers et al. (Fatty acid-binding proteins as plasma markers of tissue injury, Clinica Chimica Acta 352: 15-35 (2005)).*

Nieuwenhoven et al., Discrimination between myocardial and skeletal muscle injury by assessment of the plasma ratio of myoglobin over fatty acid binding protein, 1995, Circulation 92:2848-2854.

Gorski et al., Increased fatty acid binding protein concentration I n plasma of patients with chronic renal failure, 1997, Clinical Chemistry, 43:193-195.

Shimizu et al., Isolation and expression of a cDNA for a human brain fatty acid binding protein (B-FABP), 1997, Biochimica et Biophysica Acta 1354:24-28.

Fujii et al., Increased renal fatty acid binding protein in spontaneously hypertensive rats, Journal of Hypertension . 1988, 6:671-675.

Fujii et al., Fatty acid binding protein in kidney of normotensive and genetically hypertensive rats, Hypertension. 1987, 10:93-99.

Glossary of Terms from the National Stroke Association website, www.stroke.org, printed Aug. 11, 2001, pp. 1-7 as printed.

L. Pu et al., Expression of fatty acid binding proteins is altered in aged mouse brain, Molecular and Cellular Biochemistry 1999; 198: 69-78.

M. Takahashi et al., Rapid and sensitive immunoassay for the measurement of serum S100B using isoform-specific monoclonal antibody, Clin. Chem. 1999; 45:1307-11.

M. Robers et al., Development of a rapid microparticle-enhanced turbidimetric immunoassay for plasma fatty acid-binding protein, an early marker of acute myocardial infarction, Clin. Chem. 1998; 44:1564-1567.

A. Schreiber et al., 1998, Recombinant human heart-type fatty acid binding protein as standard in immunochemical assays, Clin. Chem Lab Med 1998; 36: 283-288.

U. Missler et al., S100 protein and neuron-specific enolase concentrations in blood as indicators of infarction volume and prognosis in acute ischemia stroke, Stroke 1997, 28:1956.

F. Shimizu et al., Isolation and expression of a cDNA for human brain fatty acid binding protein (B-FABP), Biochim. Biophys. Acta 1997, 1354:24-28.

J. Ishii et al., *Serum concentrations of myoblobin* vs. *human heart-type cytoplasmic fatty-acid binding protein in early detection of acute myocardial infarction*, Clinical Chemistry 1997, 43: 1372-1378.

W. Roos et al., Monoclonal antibodies to human heart type fatty acid-binding protein, J. Immunol. Methods 1995, 183 149-153.

E. R. Hendrickson et al., High sensitivity multianalyte immunoassay using covalent DNA-labeled antibodies and polymerase chain reaction, Nucleic Acids Research 1995; 23, 522-529.

T. Sano et al., Immuno-PCR, VCH Publishers, Inc. (1995), pp. 458-460.

P.A. Sellner et al., Development role of fatty acid binding proteins in mouse brain, Dev. Brain Res. 1995, 89:33-46.

J.M. Murphy et al., Performance of screening and diagnostic tests, Arch. Gen. Psychiatry, 1987, 44:550-555.

International Search Report, PCT/EP00/12227, filed Apr. 12, 2000.

* cited by examiner

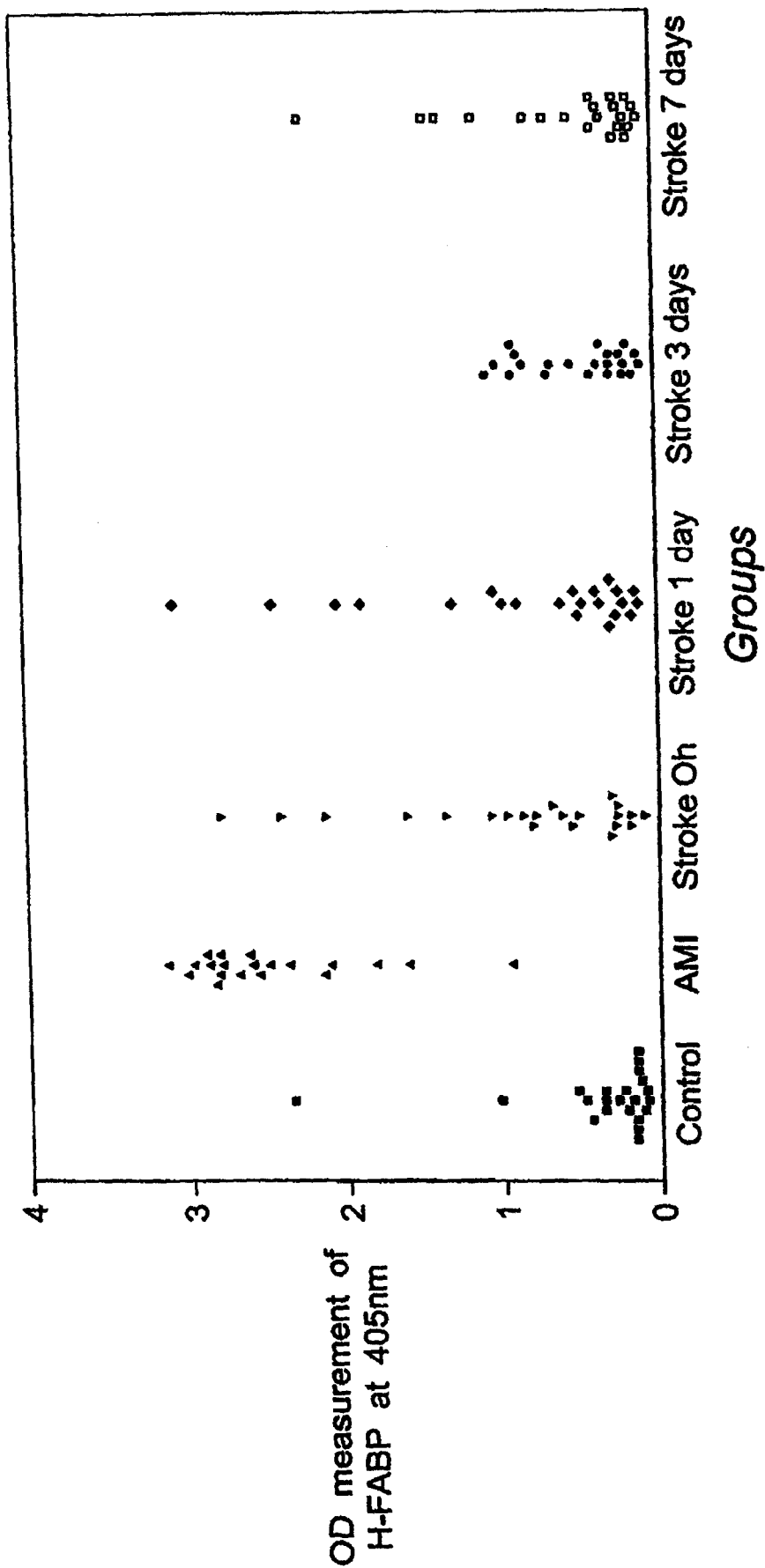

DIAGNOSTIC ASSAY FOR STROKE

This application is a continuation-in-part of application Ser. No. 10/165,127 filed Jun. 7, 2002, now U.S. Pat. No. 7,144,705, which is a continuation of International Patent Application No. PCT/EP00/12227, filed Dec. 4, 2000 and published on Jun. 14, 2001 as WO 01/42793, which claims priority to British Application No. 99 29140.3 filed Dec. 10, 1999 the contents of which are incorporated by reference in their entirety.

BACKGROUND OF THE INVENTION

1. Field of the Invention

This invention is in the field of diagnostic assay using a protein or an antibody thereto.

2. Description of the Related Art

Stroke has the third highest death-rate in industrial countries. It results from either a permanent or a transient reduction in cerebral blood flow. This reduction in flow is, in most cases, caused by the arterial occlusion due to either an embolus or a local thrombosis. Depending on the localisation of brain injury and the intensity of necrosed neurones, stroke symptoms can become a life handicap for patients and the death rate from stroke events approaches 30%.

Recently, S100B was described as a potential biochemical marker for stroke diagnosis, see U. Missler et al., "S100 protein and neuron-specific enolase concentrations in blood as indicators of infarct volume and prognosis in acute ischemia stroke", Stroke 1997; 28:1956-60. However, S100B has also been reported as a useful marker for early detection of metastases of melanoma and cerebral complications from head injury and cardiac surgery. Thus, the sensitivity and specificity of the S100B test were limited to 44% and 67%, respectively, see M. Takahashi et al., "Rapid and sensitive immunoassay for the measurement of serum S100B using isoform-specific monoclonal antibody", Clin. Chem. 1999; 45:1307-11. Development of new stroke markers would help clinicians to establish early diagnosis and thus to avoid a potential relapse of the patient.

SUMMARY OF THE INVENTION

It has now surprisingly been found that two fatty acid binding proteins (FABP), known as heart (H-FABP) and brain (B-FABP), are markers for stroke. Thus, the invention provides a method of diagnostic assay for stroke or the possibility thereof in a sample of body fluid taken from a patient suspected of suffering from a stroke, which comprises determining the concentration of heart or brain fatty acid binding protein (H-FABP or B-FABP) in the sample. The concentration thus determined is used to make or assist in making a diagnosis.

Conveniently the method is carried out using an antibody to H-FABP or B-FABP, whereby the extent of the reaction between the antibody and the FABP in the sample is assayed and related to the concentration of FABP in the sample.

The present invention enables an assay of high sensitivity, specificity and predictive positive value for stroke to be carried out. "Sensitivity" is defined as the percentage of true positives given by the assay on samples taken from patients in whom clinical examination has confirmed stroke. It is reckoned as % True positives/(True positives+False negatives). "Specificity" means the percentage of true negatives given by the assay on control samples, i.e. from patients in whom clinical examination has not revealed stroke. It is reckoned as % True negatives/(False positives+True negatives). "Predictive positive value" means the ratio % True positives/(True positives+False positives).

H-FABP is a known marker of acute myocardial infarction (AMI), see J. Ishii et al., "Serum concentrations of myoglobin vs human heart-type cytoplasmic fatty-acid binding protein in early detection of acute myocardial infarction", Clinical Chemistry 1997; 43 1372-1378. Therefore, in order to use an assay for H-FABP for stroke to better advantage, it is desirable to perform another kind of assay for AMI (one in which the marker is not a FABP) in order to eliminate from the diagnosis for stroke those patients who are positive in the AMI assay.

Thus, in a particular embodiment, the invention provides a method which comprises determining the concentration of H-FABP in a first assay, as defined above, whereby a positive result indicates the possibility of either a stroke or acute myocardial infarction, and which further comprises carrying out a second diagnostic assay, for acute myocardial infarction (AMI) only, whereby a positive result in the H-FABP assay and a negative result in the assay for AMI indicates that the patient might be suffering from a stroke. Assays using Troponin-I and Creatine Kinase-MB (CK-MB) as early biochemical markers of acute myocardial infarction (AMI) are well known and suitable for the above purpose. They can be carried out in plasma, serum or blood. Of course, the terms "first" and "second" are merely convenient labels: the two assays can be carried out in either order.

A similar H-FABP and also a brain-specific fatty acid binding protein (B-FABP) have been found in the brain of mice, see L. Pu et al., Molecular and Cellular Biochemistry 1999; 198 69-78. Brain H-FABP (not to be confused with B-FABP) is believed to differ from heart H-FABP by a single amino acid substitution. However, B-FABP differs considerably. P. A. Sellner et al., "Development role of fatty acid binding proteins in mouse brain" Dev. Brain Res. 1995; 89:33-46 estimated the DNA homology at 69%, while A. Schreiber et al., "Recombinant human heart-type fatty acid binding protein as standard in immunochemical assays" mention 64% amino acid sequence homology and that a monoclonal antibody to human H-FABP is cross-reactive with human B-FABP to the extent of only 1.7%.

Now that the present inventors have found that H-FABP is a marker for stroke, it is a very reasonable prediction that B-FABP will also be. Since B-FABP is specific to brain tissue and does not appear to react significantly with a monoclonal antibody to H-FABP, it will not give positives for AMI, making a separate assay for AMI unnecessary.

BRIEF DESCRIPTION OF THE DRAWING

The sole FIGURE is a graphic representation on the y-axis of H-FABP concentration represented by optical density measurement at 405 nm, as determined by the method of the invention, for (a) the control group having neither stroke nor AMI (b) the group having AMI and (c) the stroke group, at four time points after admission (0 hours, 1 day, 3 days and 7 days).

DESCRIPTION OF PREFERRED EMBODIMENTS

For the method of assay, the sample can be taken from the blood, plasma or serum of the patient. The marker, H-FABP or B-FABP, is preferably measured by an immunoassay, using a specific antibody to H-FABP and measuring the extent of the antigen (H-FABP or B-FABP)/antibody interaction. For the diagnosis of human patients, the antibody is preferably anti-human H-FABP or B-FABP. Similarly, if the patient is an animal the antibody should be to the H-FABP or B-FABP of the same animal variety, e.g. anti-equine H-FABP or B-FABP if the patient is a horse. It may be a monoclonal antibody or an engineered antibody. Conveniently a mouse anti-human, anti-equine etc. monoclonal antibody is used. Antibodies to H-FABP are known, e.g. 66E2 and 67D3 described by W. Roos et al., "Monoclonal antibodies to human heart type fatty acid-binding protein", J. Immunol. Methods 1995; 183 149-153, are commercially available.

Antibodies specific for B-FABP are also known. Kurtz et al. (Development, 1994, 120: 2637-2649; incorporated herein by reference) describe the production of a rabbit polyclonal antibody using a recombinant B-FABP expressed in *E. coli* (page 2638, column 2, lines 30-37). These antibodies were shown to be highly specific for B-FABP with no cross-reactivity for H-FABP (page 2640, FIG. 3). Using these antibodies, Kartz et al. were able to detect B-FABP expressed in several regions of rodent brain (page 2642, FIG. 6) by immunohistochemistry, which may be deemed a form of immunoassay. Godbout et al. (Oncogene, 1998, 16: 1955-1962; incorporated herein by reference) describe the production of B-FABP specific antibodies by immunising rabbits with chick retina fatty acid binding protein, which has high homology with mouse brain B-FABP (page 1957, column 2, lines 23-27). B-FABP was then detected in cytoplasmic extracts of human malignant glioma cells by Western blotting, another form of immunoassay (page 1961, column 2, lines 14-24; page 1958, FIG. 5). Myers-Payne et al. (J. Neurochem., 1996, 66, 1648-1656; incorporated herein by reference) describe Western blot experiments using antibodies specific for recombinant mouse heart H-FABP and recombinant mouse brain B-FABP wherein native mouse brain B-FABP was selectively bound by the anti-recombinant mouse brain B-FABP and not the anti-recombinant mouse heart H-FABP (see FIG. 6). This paper therefore clearly teaches immunological reagents and an immunoassay for B-FABP.

Also, the usual Köhler-Milstein method may be used to raise additional H-FABP or B-FABP specific antibodies. The source of protein for this purpose can be the naturally derived or recombinant DNA-prepared protein. Recombinant human H-FABP and B-FABP have been described by A. Schreiber supra and F. Shimizu et al., "Isolation and expression of a cDNA for human brain fatty acid binding protein (B-FABP)", Biochim. Biophys. Acta 1997; 1354:24-28, respectively. Less preferably, the antibody may be polyclonal.

Any known method of immunoassay may be used. A sandwich assay is preferred. In this method, an antibody (e.g. polyclonal) to the FABP is bound to the solid phase such as a well of a plastics microtitre plate, and incubated with the sample and with a labelled second antibody specific to the H-FABP or B-FABP to be detected. Alternatively, an antibody capture assay (also called "indirect immunoassay") could be used. Here, the test sample is allowed to bind to a solid phase, and the anti-FABP antibody (polyclonal or monoclonal) is then added and allowed to bind. If a polyclonal antibody is used in this context, it should desirably be one which exhibits a low cross-reactivity with other forms of FABP. After washing away unbound material, the amount of antibody bound to the solid phase is determined using a labelled second antibody, anti- to the first.

A direct assay could be performed by using a labelled anti-FABP antibody. The test sample is allowed to bind to the solid phase and the anti-FABP antibody is added. After washing away unbound material, the amount of antibody bound to the solid phase is determined. The antibody can be labelled directly rather than via a second antibody.

In another embodiment, a competition assay could be performed between the sample and a labelled FABP or a peptide derived therefrom, these two antigens being in competition for a limited amount of anti-FABP antibody bound to a solid support. The labelled FABP or peptide could be pre-incubated with the antibody on the solid phase, whereby the FABP in the sample displaces part of the FABP or peptide thereof bound to the antibody.

In yet another embodiment, the two antigens are allowed to compete in a single co-incubation with the antibody. After removal of unbound antigen from the support by washing, the amount of label attached to the support is determined and the amount of protein in the sample is measured by reference to standard titration curves established previously.

Throughout, the label is preferably an enzyme. The substrate for the enzyme may be colour-forming, fluorescent or chemiluminescent. Alternatively, the label may be a radioisotope or fluorescent, e.g. using conjugated fluorescein.

The enzyme is preferably alkaline phosphatase or horseradish peroxidase and can conveniently be used colorimetrically, e.g. using p-nitrophenyl phosphate as a yellow-forming substrate with alkaline phosphatase.

For a chemiluminescent assay, the antibody can be labelled with an acridinium ester or horseradish peroxidase. The latter is used in enhanced chemiluminescent (ECL) assay. Here, the antibody, labelled with horseradish peroxidase, participates in a chemiluminescent reaction with luminol, a peroxide substrate and a compound which enhances the intensity and duration of the emitted light, typically 4-iodophenol or 4-hydroxycinnamic acid.

An amplified immunoassay such as immuno-PCR can be used. In this technique, the antibody is covalently linked to a molecule of arbitrary DNA comprising PCR primers, whereby the DNA with the antibody attached to it is amplified by the polymerase chain reaction. See E. R. Hendrickson et al., Nucleic Acids Research 1995; 23, 522-529 (1995) or T. Sano et al., in "Molecular Biology and Biotechnology" ed. Robert A. Meyers, VCH Publishers, Inc. (1995), pages 458-460. The signal is read out as before.

In a particularly preferred procedure, an enzyme-linked immunosorbent assay (ELISA) was developed to detect H-FABP. Since H-FABP is a marker for AMI as well, Troponin-I or CK-MB concentrations were assayed in order to exclude any heart damage. As described in the Example, These assays were assessed in serial plasma samples, from 22 patients lacking AMI and stroke, 20 patients with AMI and 22 patients with confirmed stroke at four times points after the admission at the medical centre. The sensitivity, specificity and predictive positive value for H-FABP in stroke were 59.1%, 90.9% and 86.7% respectively. Only one out of 22 stroke patients had increased H-FABP and Troponin-I expression. Thus, H-FABP detection combined with the Troponin-I or CK-MB assay provide a useful marker of stroke diagnosis or brain damage.

The use of a rapid microparticle-enhanced turbidimetric immunoassays, developed for H-FABP in the case of AMI, M. Robers et al., "Development of a rapid microparticle-enhanced turbidimetric immunoassay for plasma fatty acid-binding protein, an early marker of acute myocardial infarction", Clin. Chem. 1998; 44:1564-1567, should drastically decrease the time of the assay. Thus, the full automation in a widely used clinical chemistry analyser such as the COBAS™ MIRA Plus system from Hoffmann-La Roche, described by M. Robers et al. supra, or the AxSYM™ system from Abbott Laboratories, should be possible and applied for routine clinical diagnosis of stroke.

The H-FABP or B-FABP concentrations can be measured by other means than immunoassay. For example, the sample can be subjected to 2D-gel electrophoresis and the amount of the FABP estimated by densitometric scanning of the gel or of a blot therefrom. However, it is desirable to carry out the assay in a rapid manner, so that the patient can be treated promptly.

The following Example illustrates the invention.

EXAMPLE

Materials and Methods

Patients

The study population consisted of 22 age-and-gender matched control patients (Control group), 20 confirmed AMI patients (AMI group) and 22 confirmed stroke patients (Stroke group). The Control group included 14 men, mean age 66, range 34-86 years, and 8 women, mean age 63, range 51-81 years. The AMI group included 16 men, mean age 65, range 29-90 years, and 4 women, mean age 72, range 66-81 years. The Stroke group included 14 men, mean age 65, range 30-87 years, and 8 women, mean age 64, range 51-85 years. Four blood samples were collected for each patient of the Stroke group after admission ($t_0$=0 h; $t_1$=1 day, $t_3$=3 days, $t_7$=7 days). Blood samples were collected in dry heparin-containing tubes. After centrifugation at 1500 g for 15 min at 4° C., the plasma samples were stored as aliquots at −20° C. until analysis. Patients from the Stroke group underwent serial clinical evaluations by neurologists in order to confirm stroke diagnosis. Patients from AMI group were admitted to the hospital with a confirmed AMI (Troponin-I concentration>2 ng/ml). A clinical evaluation was performed on all the patients from the control group to exclude Stroke and AMI.

Measurement of Brain and Heart H-FABP

H-FABP concentrations were measured in plasma by a sandwich ELISA. A 96-well polystyrene microplate (NUNC) was coated with 100 μl/well polyclonal goat anti human muscle-FABP (Spectral Diagnosis HC, Ontario, USA), 20.4 ng/ml in carbonate buffer 0.1M pH 9.6, overnight at 4° C. The plate was automatically washed with PBS (15 mM $Na_2PO_4$-120 mM NaCl-2.7 mM KCl pH 7.4, Sigma) on a BioRad NOVAPATH™ washer. Every washing step was performed with fresh PBS. Non-specific binding sites were blocked with 200 μl/well 2% casein in carbonate buffer for 2 h at 37° C. After the washing step, the samples were pipetted in duplicate at 100 μl/well. The plate was incubated 2 h at 37° C. After the washing step, 100 μl/well of mouse anti-human Heart FABP (clone 66E2, HyCult Biotechnology BV, Uden, Netherlands), 0.3 ng/ml in PBS-1% BSA, were incubated for 1 h at room temperature (R.T.) with shaking. After the washing step, 100 μl/well of phosphatase-labelled anti-mouse immunoglobulin (Dako, Denmark), 15 ng/ml in PBS, were incubated 1 h 30 min at R.T. with shaking. After the washing step, 50 μl/well of phosphatase substrate, 1.5 mg/ml para-nitrophenylphosphate in diethanolamine, were incubated 30 min. The reaction was stopped with 100 μl/well 1M NaOH. Colour development was measured with a microplate reader at a wavelength of 405 nm.

CK-MB and Troponin-I Measurement

AMI was diagnosed by clinical evaluation and Troponin-I and CK-MB measurements. Samples were centrifuged at 1500 g for 15 min, and stored at −20° C. Serum CK-MB and Troponin-I concentrations were determined using a fluorescent microparticle enzyme immunoassay (MEIA) with an automated chemical analyser AxSYM™ system (Abbott Laboratories, Abbott Park, Ill., USA). The rate of formation of fluorescent products was directly proportional to the amount of Troponin-I in the sample. The detection limit for Troponin-I was 0.3 μg/l. CK-MB measurement is proportional to the amount of fluorescent probes and the detection limit was 0.7 μg/l.

Statistical Analysis

H-FABP concentrations were expressed in optical densitometry (OD) values either as mean±SD or as median and inter-quartile range. Troponin-I and CK-MB concentrations were expressed in concentration units (ng/ml). The non-parametric Mann-Whitney U-test was used to compare in plasma H-FABP, Troponin-I and CK-MB concentrations between groups. PRISM™ software was used to elaborate box/whisker and scatter plots. The 95% confidence intervals (CI) and Receiver Operating Characteristic (ROC) curves, defined by Analyse-It™ software for Microsoft EXCEL™, were used to assess the discriminatory time point of the indicators. See J. M. Murphy et al., "Performance of screening and diagnostic tests", Arch. Gen. Psychiatry 1987; 44:550-555.

A univariate Z-test was used to compare the areas under the ROC curves of H-FABP. Differences in sensitivity, specificity and predictive positive value of H-FABP concentrations at each time points were evaluated. P<0.05 was considered statistically significant.

Results

Clinical Characteristics

Patients from the Stroke group were given a complete clinical evaluation. Ischaemia and haemorrhage were diagnosed with the help of computer tomographic (CT) scan and cerebral IRM response as well as their localisation (data not shown). Stroke diagnosis was confirmed for each patient from the Stroke group. Injury type and localisation did not correlate with H-FABP concentration (data not shown).

Patients from the Control group were admitted to hospital and stroke and AMI were excluded by clinical evaluation.

Patients from the AMI group were admitted to the hospital with confirmed AMI with high Troponin-I levels (>2 ng/ml).

Assay results are shown in Table 1 below.

TABLE 1

| Assay type | Control Group | AMI Group | Stroke Group | | | |
|---|---|---|---|---|---|---|
| | | | 0 h | 1 day | 3 days | 7 days |
| H-FABP | | | | | | |
| median (25-75%) OD, 405 nm | 0.19 (0.14-0.35) | 2.65 (2.27-2.86) | 0.64 (0.28-1.01) | 0.46 (0.25-0.98) | 0.37 (0.20-0.76) | 0.33 (0.18-0.73) |

TABLE 1-continued

| Assay type | Control Group | AMI Group | Stroke Group | | | |
|---|---|---|---|---|---|---|
| | | | 0 h | 1 day | 3 days | 7 days |
| Significance Troponin-1 | | *** | *** | ** | ns | ns |
| median (25-75%) IU ng/ml | 0 (0.0-0.0) | 50 (50-359) | 0 (0.0-0.3) | 0 (0.0-0.2) | | |
| Significance CK-MB | ** | ns | ns | | | |
| median (25-75%) IU ng/ml | 1 (0.7-0.12) | 63 (27-87.5) | 2.7 (1.35-4.05) | 1.6 (1.3-3.3) | | |
| Significance | ** | ns | ns | | | |

Significance:
*** p < 0.001
** p < 0.01
ns non-significant

H-FABP plasma concentrations (OD measurement) in the AMI group were significantly higher than in the Control group (Table 1). The AMI group had a H-FABP median concentration (range 25-75%) of 2.65 (2.27-2.86) while the Control group had a concentration of 0.19 (0.14-0.35). The H-FABP concentration decreases with time after the brain acute event increased. H-FABP median concentration (range 25-75%) in the Stroke group was 0.64 for $t_0$ (0.28-1.01), 0.46 for $t_1$ (0.25-0.98), 0.37 for $t_3$ (0.20-0.76) and 0.33 for $t_7$ (0.18-0.73). Some overlap exists between the inter-quartile range of the Stroke and the Control groups due to presence of false negatives. The H-FABP concentration distribution was visualised by the scatter plot of the drawing. Receiver Operating Curve plots were made of Sensitivity against Specificity at different times, namely on admission of the patient and at 1, 3 and 7 days after admission. The ROC curves were used to optimise Sensitivity and Specificity and to maximise the sum of Sensitivity and Specificity by choosing and adequate cut-off value in optical density units, representing H-FABP concentration. The plots showed that the best Sensitivity and Specificity for this group of patients was obtained on admission of the patient, with a cut-off value at OD 0.53. Under these conditions, the Sensitivity, Specificity and Predictive Positive Value of H-FABP concentrations were 59.1%, 90.9% and 86.7% respectively. Comparison between ROC curves on admission with those made at the later times did not show any enhancement of sensitivity and specificity values beyond those obtained on admission.

To confirm differences in H-FABP concentrations between AMI and Control groups, CK-MB and Troponin-I were assayed. In addition, in order to discriminate AMI and Stroke, they were also assayed on stroke samples. The Troponin-I and CK-MB concentrations were measured in each group. Troponin-I and CK-MB concentrations in the AMI group were significantly (P>0.01) higher than in the Control group. No significant differences of concentration of these indicators were found between the Control and the Stroke group. ABBOTT laboratories showed that the expected values using the AxSYM™ Troponin-I assay and the AxSYM™ CK-MB assay for AMI diagnosis are determined at the cut off 2 ng/ml and 9.3 ng/ml respectively. The CK-MB value expected for the control group is up to 3.8 ng/ml. At the Troponin-I concentration>2 ng/ml, the sensitivity and specificity of the MEIA Troponin-I assay were 93.3% and 94.4%, respectively, at $t_1$. The median Troponin-I and CK-MB concentrations (25-75%) in the plasma were calculated and are shown in Table 1.

Table 2 summaries the evaluation of the assay.

TABLE 2

| Group | Control | AMI | Stroke |
|---|---|---|---|
| No. samples | 22 | 20 | 22 |
| H-FABP (OD) | | | |
| More than 0.531 | 2 | 20 | 13 |
| 0.531 or less | 20 | 0 | 9 |
| Troponin-1 & CK-MB AMI diagnosis | | 20 | 1 |
| Myocardial suffering without AMI | | | 6 |
| Clinical anamnesis | | | |
| Stroke diagnosis | | | 22 |
| Epilepsy | 1 | | |
| Fracture | 2 | | |

In the Control group, two false positives were detected. H-FABP was increased at $t_0$ (Table 2). One of these had Troponin-I and CK-MB concentrations at the border between healthy and myocardial pain (3.8 ng/ml), indicating that this person should suffer from myocardial muscle lacking AMI. Indeed, one of these had epilepsy and both suffered from several fractures. In the Stroke group, 13 true positives were detected (10 had ischemia and 3 had haemmorage). High H-FABP concentrations were measured and stroke diagnosis was confirmed. Healthy Troponin-I and CK-MB concentrations were measured and allowed the exclusion of an AMI diagnosis, except for one patient. For this exception, clinical evaluation did not detect myocardial suffering and did not correlate with Troponin-I concentration for AMI. H-FABP measured did not allow the discrimination between brain or myocardial pain. In the stroke group, 9 false negatives were detected with low H-FABP levels (6 had ischemia and 3 haemmorage). No explanation was found for these cases. No correlation was found between low H-FABP concentration and clinical evaluation.

Discussion

The above results indicate that H-FABP is a potential marker for stroke diagnosis. Since H-FABP was presented as a marker of acute myocardial infarction few years ago, Stroke and AMI had to be discriminated by another AMI biochemical marker such as Troponin-I or CK-MB. After the discrimination of AMI for stroke patient, the serum H-FABP concentration could be used as a specific marker of stroke.

At the admission, H-FABP assay allowed a sensitivity, a specificity and a predictive positive value (OD response>0.531) of 59.1%, 90.9% and 86.7% respectively. These values were significantly higher than those of S100B protein for detection of stroke. The sensitivity and the specificity of S100B assay for stroke were of 44% and 67% respectively. The advantage of S100B analysis was the development of a rapid immunoassay less than 3 h. However, the specificity of S100B was not limited to stroke but also metastases of melanoma, cerebral complications from head injury and cardiac surgery. The kinetics of H-FABP in the blood stream were studied by measuring H-FABP at four time points after admission at the screening clinic ($t_0$ (0 h), $t_1$ (1 day), t (3 days) and $t_7$ (7 days)) for each patient with confirmed stroke. The maximum H-FABP concentrations were mostly observed at $t_0$. Variation time between brain onset and admission did not interfere with the result, because the H-FABP concentration remained elevated at $t_1$. The ROC curve area confirmed the higher H-FABP concentrations at $t_0$ and $t_1$ compared to $t_3$ and $t_7$. The best characteristics of the assay (sensitivity, specificity) were obtained at $t_0$.

Acute myocardial infarction is diagnosed with the help of a biochemical marker assay such as for cardiac Troponin-I, Creatine-Kinase MB, myoglobin and, recently, H-FABP assay. Since H-FABP concentrations could indicate AMI, discrimination between AMI and stroke was made with the use of another AMI marker.

Troponin-I is an early marker of AMI or ischemia damage, with the advantage of remaining elevated for several days following AMI. Since the concentration of Troponin-I released reaches a maximum 12-24 h after admission, the Stroke group was analysed at $t_0$ and $t_1$. The Troponin-I concentration in the AMI group was significantly higher than the cut off value of 2 ng/ml. Most of the Stroke group patients showed normal Troponin-I concentration under the cut-off value, which excluded AMI patients of the study, except for one patient. His clinical evaluation did not diagnose any myocardial suffering and this did not correlate with his Troponin-I concentration. In this one case, H-FABP measurement did not allow discrimination between brain or myocardial pain.

In parallel, the concentration of Creatine Kinase MB in plasma was measured for each patient. This marker is less specific than Troponin-I because it detects any muscle suffering types. Starting at between 2 and 6 hours after the onset of symptoms, CK-MB is released into the blood stream and its concentration therein rises until up to 18 hours after the onset of symptoms. It remains at elevated concentration until about 2 days after the onset of symptoms, after which it falls to normal.

In the Control group, two false positives were detected. One of these had epilepsy which interfere with stroke. Both fell on the floor and broke their femur and foot. Increased CK-MB correlated well with increased H-FABP. Epilepsy could explain the raised H-FABP level. H-FABP allowed a 98.6% correlation with CK-MB assay. Since Troponin-I did not allow the detection of these false positives, Troponin-I and H-FABP measurement gave a 95.3% correlation.

Each of the above cited publications is herein incorporated by reference to the extent to which it is relied on herein.

The invention claimed is:

1. A diagnostic assay for stroke comprising:
   obtaining a body fluid sample from a subject suspected of having a stroke;
   measuring the body fluid sample from the subject to determine a level of brain fatty acid binding protein contained therein;
   measuring a control sample of body fluid from subjects not suffering from stroke to determine a level of brain fatty acid binding protein contained therein; and
   comparing the level of brain fatty acid binding protein in the subject sample with the level of brain fatty acid binding protein in the control sample;
   wherein an elevated level of brain fatty acid binding protein in the sample from the subject compared to the control sample indicates that the subject is having a stroke.

2. The method of claim 1 wherein the sample is selected from the group consisting of blood, plasma and serum.

3. The method of claim 1 wherein an antibody specific for the brain fatty acid binding protein is used to detect brain fatty acid binding protein.

4. The method of claim 3 wherein the antibody is used in an immunoassay.

5. The method of claim 4 wherein the immunoassay is an enzyme-linked immunosorbent assay.

6. The method of claim 3 wherein the antibody is a monoclonal antibody.

* * * * *